(12) United States Patent
Kagan

(10) Patent No.: US 10,617,836 B2
(45) Date of Patent: Apr. 14, 2020

(54) RESPIRATORY DEVICE

(71) Applicant: Eugen Kagan, Niederkassel Lülsdorf (DE)

(72) Inventor: Eugen Kagan, Niederkassel Lülsdorf (DE)

(73) Assignee: Eugen Kagan, Niederkassel Lülsdorf ( * ) Notice: Subject to any disclaimer, the term of this patent is extended or adjusted under 35 U.S.C. 154(b) by 263 days.

(21) Appl. No.: 15/320,039

(22) PCT Filed: Jul. 6, 2015

(86) PCT No.: PCT/EP2015/065364
§ 371 (c)(1),
(2) Date: Dec. 19, 2016

(87) PCT Pub. No.: WO2016/001448
PCT Pub. Date: Jan. 7, 2016

(65) Prior Publication Data
US 2018/0177961 A1 Jun. 28, 2018

(30) Foreign Application Priority Data
Jul. 4, 2014 (DE) .................. 10 2014 109 394

(51) Int. Cl.
*A61M 16/00* (2006.01)
*A61M 16/08* (2006.01)
(Continued)

(52) U.S. Cl.
CPC ...... *A61M 16/024* (2017.08); *A61M 16/0003* (2014.02); *A61M 16/0066* (2013.01); *A61M 16/0069* (2014.02); *A61M 16/0883* (2014.02); *A61M 16/1005* (2014.02); *A61M 16/12* (2013.01); *A61M 16/125* (2014.02); *A61M 16/127* (2014.02); *A61M 16/201* (2014.02); *A61M 16/203* (2014.02); *A61M 16/208* (2013.01); *A61M 16/209* (2014.02); *A61M 2016/003* (2013.01); *A61M 2016/0027* (2013.01); *A61M 2039/0009* (2013.01);
(Continued)

(58) Field of Classification Search
CPC .......... A61M 16/0012; A61M 16/0069; A61M 16/12; A61M 16/125; A61M 16/127; A61M 2016/0027; A61M 2016/003
See application file for complete search history.

(56) References Cited

U.S. PATENT DOCUMENTS 8,047,205 B2 * 11/2011 von Blumenthal ... A61M 16/12
128/203.12
9,180,266 B1 * 11/2015 Sherman ............. A61M 16/024
(Continued)

FOREIGN PATENT DOCUMENTS

| EP | 1 064 043 A1 | 1/2001 |
| EP | 1 205 203 A1 | 5/2002 |
| WO | WO 99/36118 | 7/1999 |

*Primary Examiner* — Valerie L Woodward
(74) *Attorney, Agent, or Firm* — Pauley Erickson & Kottis

(57) ABSTRACT

A respiratory device for supplying breathing air to a patient, including an oxygen inlet to be connected to an oxygen supply, and a compressed air inlet to be connected to a compressed air supply. The respiratory device also includes a turbine for sucking in ambient air. Switching between the individual operating modes can be done automatically or manually.

25 Claims, 2 Drawing Sheets

(51) Int. Cl.
*A61M 16/12* (2006.01)
*A61M 16/20* (2006.01)
*A61M 16/10* (2006.01)
*A61M 39/00* (2006.01)

(52) U.S. Cl.
CPC .............. *A61M 2202/0208* (2013.01); *A61M 2205/3334* (2013.01); *A61M 2205/3337* (2013.01); *A61M 2205/3365* (2013.01); *A61M 2205/3368* (2013.01); *A61M 2205/3379* (2013.01)

(56) References Cited

U.S. PATENT DOCUMENTS

| | | | | |
|---|---|---|---|---|
| 2002/0053345 | A1* | 5/2002 | Jafari | A61M 16/00 128/204.23 |
| 2003/0150456 | A1* | 8/2003 | Wruck | A61M 16/12 128/204.18 |
| 2007/0175473 | A1* | 8/2007 | Lewis | A61J 11/0005 128/204.18 |
| 2008/0053441 | A1* | 3/2008 | Gottlib | A61M 16/0051 128/204.23 |
| 2009/0241960 | A1 | 10/2009 | Tunnell et al. | |
| 2010/0224192 | A1* | 9/2010 | Dixon | A61B 5/0205 128/204.23 |
| 2013/0276789 | A1 | 10/2013 | Garde et al. | |
| 2014/0216458 | A1* | 8/2014 | Asbra | A62B 9/003 128/204.16 |

* cited by examiner

RESPIRATORY DEVICE

BACKGROUND OF THE INVENTION

Field of the Invention

This invention is based on a respiratory device.

Discussion of Related Art

Conventional respiratory devices are used to supply a patient with a suitable mixture of oxygen and air in order, for example, to provide the patient with artificial respiration and/or to at least partially assist his respiration. Conventional respiratory devices always require a supply of compressed air, which must be provided by a compressed air cylinder or a stationary compressed air supply system, for example in a hospital. For this reason, in conventional respiratory devices, a mobile use, such as without a compressed air cylinder or compressed air supply system, is not possible so that in this sense, the possible uses of conventional respiratory devices are also limited to stationary operation. For mobile use, there are oxygen- or turbine-driven devices.

SUMMARY OF THE INVENTION

One object of this invention is to provide a respiratory device that does not have the disadvantages of the prior art and in particular, that enables operation in both stationary and mobile fashion without having to switch the patient to another device.

The above and other objects are attained with the respiratory device according to this invention as disclosed in this specification and in the claims.

Because in addition to compressed air and oxygen, the respiratory device is also equipped with a turbine for aspirating ambient air, both conventional stationary operation with compressed air and mobile operation using readily available ambient air are possible. The respiratory device therefore covers all possible uses.

The respiratory device can be made to assume complete responsibility for the patient's respiration. It can, however, also be made to partially assist the patient's respiration and in particular, to permit the patient to inhale independently. In the respiratory device, the oxygen from the oxygen supply is supplied either in pure form or is suitably mixed with air so that the patient can be supplied with suitable respiratory air. Accordingly, the respiratory device has an outlet and an outlet connection for the respiratory air that can be connected to the patient or to a tube system for the patient. The air mixed with oxygen can be compressed air from the compressed air supply or ambient air aspirated by the turbine.

The respiratory device can be used as an independent individual device. It can, however, also be used in connection with other medical devices, particularly in a modular application. The oxygen supply can be an oxygen cylinder and/or a stationary oxygen supply or stationary oxygen duct system, for example in a hospital. The oxygen of the oxygen supply can, for example, be at a pressure of 2.8 bar to 6.0 bar or 280 kPa to 600 kPa. The compressed air supply can be a compressed air cylinder and/or a stationary compressed air supply or stationary compressed air duct system. The compressed air can, for example, be at a pressure of 2.8 bar to 6.0 bar or 280 kPa to 600 kPa. In the context of the present application, a turbine is understood to include any suction device that is able to aspirate ambient air. It is possible, for example, for the turbine to produce a negative pressure of approx. 150 mbar or 15 kPa.

The oxygen flows or travels from the oxygen supply via the oxygen inlet through an oxygen duct into the respiratory device. The respiratory device can have a pressure sensor that measures the pressure of the oxygen in the oxygen duct.

According to one embodiment of this invention, the respiratory device has a respective pressure sensor in both the oxygen duct, for example at the inlet of the oxygen duct, and in the compressed air duct, for example at the inlet of the compressed air duct. This has one advantage of making it possible to monitor both ducts so that a failure or disconnection of the compressed air and/or oxygen can be immediately compensated for by activating of the turbine. The turbine thus compensates not only for the failed compressed air, but also if needed, for a failed oxygen supply. This is particularly advantageous in an alternate embodiment because manually switching the patient between the mobile and stationary device can take up to 15 minutes, for example. In a mobile application in which no compressed air is available, for example, if a compressed oxygen cylinder has to be replaced, then the time until the new oxygen is available can be automatically bridged by activating the turbine, thus enabling the artificial respiration of the patient to continue. A connected compressed air supply can also be used as a backup in the event that the turbine fails. If it is not possible to provide a compressed air supply by compressed air and the turbine, then the artificial respiration is carried out with oxygen.

The respiratory device can have a metering valve with which the oxygen in the oxygen duct can be metered and the flow of oxygen through the oxygen duct can be regulated. In addition, the respiratory device can have a flow rate sensor, which measures the flow rate of the oxygen through the oxygen duct. In addition to acting on the respiratory device via the oxygen duct, it is also possible to run the turbine in order to supply additional ambient air.

If a compressed air supply is connected, the compressed air flows via the compressed air inlet, through a compressed air duct, and into the respiratory device. The respiratory device can have another pressure sensor that measures the pressure of the compressed air in the compressed air duct. The respiratory device can have another metering valve with which the compressed air in the compressed air duct can be metered and the flow of compressed air through the compressed air duct can be regulated. In addition to the compressed air, oxygen can be supplied via the oxygen duct.

Advantageous embodiments and modifications of this invention are disclosed by the claims and the specification taken in conjunction with the drawings.

In the respiratory device, oxygen, compressed air, and/or aspirated ambient air are mixed with one another. This can take place in the duct system of the respiratory device.

According to one embodiment, however, the respiratory device has a mixing chamber. In the mixing chamber, for example, the oxygen from the oxygen supply is mixed with the compressed air from the compressed air supply or with the aspirated ambient air. Particularly when aspirating ambient air with the turbine, it is possible to regulate the flow rate of the air directly by the turbine so that it is advantageously possible to do without a pressure reservoir, making it possible to significantly simplify the design of the respiratory device.

In particular, it is possible for the flow rate of the aspirated ambient air to be regulated via the speed of the turbine. Depending on the required flow rate of the aspirated ambient air, it is advantageously possible to change the speed of the turbine so that at times of high demand, the speed of the turbine can be increased, and at times of low demand, the speed of the turbine can be decreased. In particular, it is possible for the pressure, the flow pattern, and/or the volume of the aspirated air to be adjusted by the turbine. In particular, these parameters can be adjusted via the speed of the turbine. This significantly simplifies the design of the respiratory device.

In one embodiment, the respiratory device has an oxygen inlet for connecting to an oxygen supply, with the oxygen being able to flow via the oxygen inlet, through an oxygen duct toward a mixing chamber, and has a compressed air inlet for connecting to a compressed air supply, with the compressed air being able to flow via the compressed air inlet through a compressed air duct toward the mixing chamber. The respiratory device also has a turbine for aspirating ambient air, where aspirated ambient air can flow through an ambient air duct from an inlet opening toward the mixing chamber. The compressed air duct and/or the ambient air duct can be connected to oxygen to form a shared air duct if oxygen is present. Otherwise, artificial respiration is provided with air alone. If a mixing chamber is provided, then the ducts can be connected to one another upstream of the mixing chamber or can feed separately from one another into the mixing chamber. The respiratory device has a metering valve for metering the oxygen supplied via the oxygen inlet. The metering valve and the turbine are connected via a control loop to a first pressure, and/or flow rate meter for measuring the oxygen pressure, and/or flow rate through the oxygen duct and to a second pressure and/or flow rate meter for measuring the air pressure and/or flow rate through the air duct. The metering valve and the turbine can be controlled as a function of the measured oxygen pressure and/or flow rate and the measured air flow rate.

Since pressure sensors are provided both at the oxygen inlet and at the compressed air inlet, making it possible to monitor the pressure at the oxygen inlet and/or compressed air inlet, the metering valve and the turbine can be controlled as a function of the measured oxygen pressure and the measured air pressure.

This has one advantage that the regulation of the respiratory device is carried out by the respective flow rates or the individual duct pressures and a pressure reservoir is not required. This is particularly advantageous when it comes to being able to use the respiratory device in a mobile fashion because a pressure reservoir is technically complex and also requires a relatively large amount of space.

It is also possible for the adjustments of the flow rate, pressure, flow pattern, and/or volume of the aspirated air to be controlled by a microprocessor, it being possible for the adjustments to be manually preset by the user or automatically preset by a selected artificial respiration mode. The microprocessor permits an exact control of the above-mentioned parameters. It also significantly increases flexibility in the use of the respiratory device.

In particular, the respiratory device can automatically switch between stationary and mobile operation. A sequence or priority can be automatically established among the three operating modes of compressed air, turbine, and oxygen. It is also possible, however, to carry out the switching manually. For this purpose, pressure sensors are provided, which are allocated to the oxygen inlet and the compressed air inlet in order to monitor the prevailing inlet pressure for oxygen and/or compressed air. If a pressure drop occurs, for example because connected pressure cylinders are empty or because supply ducts have been disconnected, such as in order to move a patient, then the control unit automatically switches the turbine on in reaction to the detected pressure drop in order to continue artificial respiration. Naturally, this automatic mechanism can be switched off and the turbine can also be switched on manually.

The respiratory device therefore is capable of determining whether compressed air and/or oxygen are connected and whether they have enough pressure. A control unit of the respiratory device stores a programming code that initiates the automatic selection of the operating mode. For example, the selection can be made based on whether oxygen and/or compressed air are connected and operationally ready, the demand for respiratory air, or a manual input by a user. For example, it is possible for the artificial respiration with compressed air and oxygen to have first priority, but for an artificial respiration with aspirated ambient air and oxygen to be resorted to as a second priority if no compressed air is connected. If no oxygen is connected, then as a second priority, an artificial respiration exclusively with compressed air can take place or with a third priority, an artificial respiration exclusively with aspirated ambient air can be carried out when no compressed air is connected either.

A user can cancel this automatic selection by making a manual entry. For example, he can choose for an artificial respiration to take place exclusively with oxygen, even though compressed air is available or the turbine is operational.

The automatic selection with the possibility of canceling or changing the selection manually has the advantage that the respiratory device provides suitable respiratory air in every situation, without time being consumed for the switching. It is therefore particularly suitable for mobile use and for switching between the various application purposes.

It is also advantageously possible for the gas mixture of air and oxygen to be conveyed through an outlet duct to the outlet of the respiratory device. It is also advantageously possible for the respiratory device to have another flow rate sensor, which measures the flow rate of respiratory air in the outlet duct. In addition, the respiratory device can have a temperature sensor and/or a pressure sensor with which it is possible to measure the temperature and/or pressure of the respiratory air in the outlet duct. It is thus advantageously possible to continuously monitor whether the mixed respiratory air is suitable for the patient.

As described above, the respiratory device can be selectively operated in one of three operating modes (turbine (optionally with oxygen), compressed air (optionally with oxygen), and oxygen). A user can select the operating modes. In the first operating mode, the turbine aspirates ambient air and no compressed air is supplied and in the second operating mode, compressed air is supplied from the compressed air supply and the turbine is switched off. It is thus advantageously possible, depending on the intended application purpose, for the user of the respiratory device to select the first or the third operating mode when a mobile use of the respiratory device is desired and for example a compressed air supply is not available. In this first operating mode, the metering valve in the compressed air duct is closed so that no air can flow through the compressed air duct. In the first operating mode, the entire air supply is ensured by the turbine so that the respiratory device can be operated self-sufficiently and independently of stationary compressed air supplies or compressed air cylinders. It is thus possible to significantly expand the possible uses of the respiratory device. It is possible as needed to add oxygen such as from a pressure cylinder, in both operating modes.

Alternatively, the respiratory device can be operated in the second operating mode, for example if a stationary compressed air supply is available. In the second operating mode, the turbine is switched off so that it is advantageously possible to conserve the energy supply of the turbine when a stationary compressed air supply is available. The operation of the respiratory device in these two operating modes and the variable option for the user to select one of the two operating modes depending on the intended application permit a flexible possible use of the respiratory device and significantly increase the scope of application of the respiratory device. It is also possible, however, to use compressed air and the turbine in parallel if this seems necessary. This is implemented on the control unit end in that the compressed air inlet, oxygen inlet, and turbine can be switched individually and independently of one another and in addition, can be united in meaningful combinations that can be called up in the form of operating programs.

The respiratory device can also be used in the third operating mode in which it is only connected to the oxygen supply. No compressed air is connected to the compressed air inlet. In addition, the turbine is switched off.

If a pressure drop is detected at the pressure sensor, the turbine can be automatically switched on in order to continue the artificial respiration, for example when disconnecting the compressed air when transporting the patient.

According to another embodiment, a metering valve for metering the supplied oxygen via the oxygen inlet and the turbine is connected via a control loop to a first flow rate meter for measuring the oxygen flow rate and a second flow rate meter for measuring the air flow rate, with the metering valve and the turbine being controlled as a function of the measured oxygen flow rate and the measured air flow rate. The regulation is carried out by measuring the flow rates and, depending on these values, controlling the metering valve and/or turbine in order to achieve the desired pressure, volume, flow pattern, and/or oxygen concentration in the respiratory air for the patient. The control loop advantageously makes it possible to continuously monitor the flow rates and continuously readjust the turbine and metering valve in order to consistently obtain a suitable composition of respiratory air and in particular a suitable concentration of oxygen.

As mentioned above, the regulation can alternatively also be carried out by the pressure meter instead of by the flow rate meter.

According to another embodiment, the respiratory device has a check valve that permits an air flow from the turbine toward the mixing chamber and prevents an air flow from the mixing chamber toward the turbine. It is thus advantageously possible to permit the patient to spontaneously inhale during the exhalation phase of the device. In addition, when operating in the second operating mode, it is possible to prevent an escape of compressed air via the turbine.

According to another embodiment, the respiratory device has an emergency evacuation device, which in the event of an excess pressure in the respiratory device, can discharge the excess pressure, for example, from the outlet duct. It is thus advantageously possible to prevent the occurrence of pressures that are hazardous to the patient, which pressures can be produced when using pressurized oxygen and/or compressed air. The emergency evacuation device can, for example, have a pressure relief valve positioned in the outlet duct, which is opened by a control valve so that excess pressure can escape from the outlet duct.

According to another embodiment, the respiratory device has a venturi nozzle, which is configured so that the oxygen from the oxygen inlet flows through the venturi nozzle either via the high-pressure line (oxygen cylinder or central oxygen supply in the hospital) or via the low-pressure line (oxygen concentrator) and thus produces a negative pressure so that ambient air is aspirated and is supplied for mixing with the oxygen. In particular, it is also possible, for example, to operate the respiratory device in a third operating mode, such as in addition to the first and second operating modes. In the third operating mode, the turbine is switched off and the compressed air supply is closed so that the air is supplied exclusively via the ambient air aspirated via the venturi nozzle.

The venturi nozzle can be positioned in the oxygen duct if a mixing chamber is provided, for example upstream of the mixing chamber. In this third operating mode, it is advantageously possible to do without with a compressed air supply and it is not necessary to operate the turbine. This third operating mode is therefore suitable for mobile use without the stationary compressed air supply and does not require any energy for the turbine. The third operating mode thus enables a flexible and mobile use that consumes comparatively little energy and significantly expands the possible uses of the respiratory device. The supply of the oxygen through the venturi nozzle can be controlled by another metering valve and the supply of the aspirated air can be controlled by another metering valve. Among other things, the pressure ratios in the venturi nozzle determine the quantity of aspirated air and thus the oxygen concentration in the mixing chamber.

Exemplary embodiments of this invention are shown in the drawings and will be explained in greater detail in the following description.

DETAILED DESCRIPTION OF THE INVENTION

Figure 1:
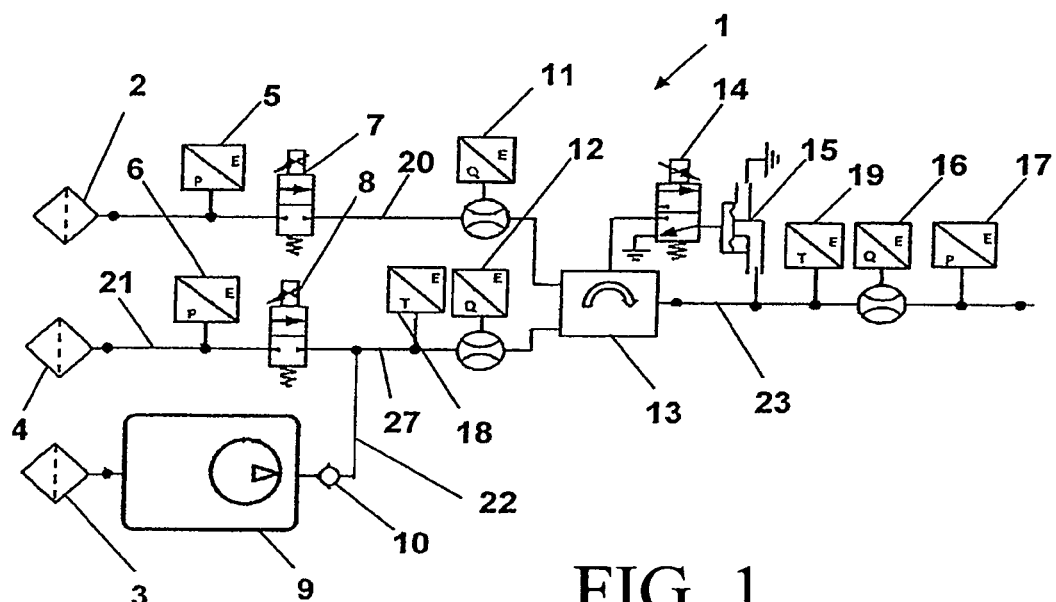
FIG. 1 is a respiratory device according to one embodiment of this invention.

In the different figures, parts that are the same are always provided with the same reference numerals and thus are also named or mentioned only once.

FIG. 1 schematically shows a respiratory device 1 according to one embodiment of this invention. The respiratory device 1 has an oxygen inlet 2. The oxygen inlet 2 is connected, for example, to oxygen at a pressure of for example 2.8 to 6.0 bar or. 280 to 600 kPa. It is also possible to provide a low-pressure oxygen supply (from the oxygen concentrator). It is possible to switch between these alternative oxygen supplies manually or automatically. This oxygen supply can, for example, be provided by an oxygen cylinder or a central oxygen supply or by the low-pressure oxygen duct from the oxygen concentrator. The oxygen flows in an oxygen duct 20 from the oxygen inlet 2 toward a mixing chamber 13, into which the oxygen duct 20 feeds. Downstream of the oxygen inlet 2 in the oxygen duct 20, the respiratory device 1 has a pressure sensor 5, which measures the inlet pressure of the oxygen. In the oxygen duct 20, the respiratory device 1 has a metering valve 7, with which it is possible to meter the oxygen. The respiratory device 1 has a flow rate sensor 11, which measures the flow rate of the oxygen through the oxygen duct 20.

The respiratory device 1 has an intake opening 3, which is provided with a filter and is used to aspirate ambient air. The ambient air flows through an ambient air duct 22 from the intake opening 3 toward the mixing chamber 13. The ambient air is aspirated by a turbine 9. The turbine 9 produces a negative pressure of approx. 150 mbar or 15 kPa. As viewed in the flow direction of the ambient air, a check valve 10 is provided downstream of the turbine 9. The check valve 10 opens only for an air flow from the turbine 9 toward the mixing chamber 13, such as the check valve 10 is closed for a flow from the mixing chamber 13 toward the turbine 9 and does not permit any flow in this direction.

The respiratory device 1 has a compressed air inlet 4 to which compressed air is connected, for example, at a pressure of 2.8 to 6.0 bar or 280 to 600 kPa. This compressed air supply can, for example, be provided by a compressed air cylinder or a central compressed air supply. The compressed air flows through a compressed air duct 21 from the compressed air inlet 4 toward the mixing chamber 13. Downstream of the compressed air inlet 4 in the compressed air duct 21, the respiratory device 1 has a pressure sensor 6, which measures the inlet pressure of the compressed air. The respiratory device 1 has a metering valve 8 in the compressed air duct 21, which can be used to meter the supply of compressed air.

The compressed air duct 21 connects to the ambient air duct 22 to form a shared air duct 27. The respiratory device 1 has a temperature sensor 18, which measures the temperature of the air in the air duct 27. The respiratory device 1 has a flow rate sensor 12, which measures the flow rate of the air in the air duct 27. The oxygen duct 20 and the air duct 27 feed into the mixing chamber 13.

The gas mixture exits the mixing chamber 13 by an outlet duct 23, which leads from the mixing chamber 13 to the patient or more precisely to the connection for the tube system for the patient. The respiratory device 1 has a control valve 14 and a pressure relief valve 15. The control valve 14 is used to control the pressure relief valve 15. The respiratory device 1 has a temperature sensor 19, which measures the temperature of the gas mixture in the outlet duct 23 after it exits the mixing chamber 13. The respiratory device 1 has a flow rate sensor 16, which measures the flow rate of the gas mixture in the outlet duct 23. The respiratory device 1 has a pressure sensor 17, which measures the pressure of the gas mixture at the patient connection port.

The respiratory device 1 can be operated in a first operating mode in which the respiratory device 1 is connected by the oxygen inlet 2 to the oxygen supply and ambient air is aspirated via the turbine 9 at the intake opening 3. In this operating mode, the metering valve 8 is closed so that the compressed air duct 21 is closed. The metering valve 7 and the turbine 9, for example with the aid of a microprocessor, not shown, administer the desired pressure, flow pattern, volume, and oxygen concentration directly to the patient. These parameters can be either manually set by the user or automatically preset by the selected artificial respiration mode.

In order to be able to correctly apply the flow pattern and oxygen concentration, the metering valve 7 and the turbine 9 together with the flow rate sensors 11 and 12 form a multi-stage control loop. The oxygen concentration is determined by an oxygen content measuring cell/sensor and/or by the ratio of the measured pressures and flow rates of the flow rate sensors 11 and 12. The total flow is determined by the sum of the measured pressures and flow rates of the flow rate sensors 11 and 12. In order to be able to use the correct pressure curve, the metering valve 7 and the turbine 9 together with the pressure sensor 17 form an additional control loop. The mixing chamber 13 only is only used for improved mixing of oxygen and air and in particular, does not form or constitute a pressure reservoir. The gas that is contained in the mixing chamber and supplied to the patient is thus not yet regulated to a constant, preset pressure. Instead, the regulation is carried out by the pressure sensors 5 and 6 and/or by the flow rate sensors 11 and 12. Since the turbine 9 is designed for dynamic operation and can thus produce the required flow and pressure, a pressure reservoir is not needed.

In a second operating mode of the respiratory device 1, instead of being taken from the ambient air, the air is supplied from a compressed air cylinder or a central air supply, which is connected to the compressed air inlet 4. In this operating mode, the turbine 9 is switched off so that no air can flow through the ambient air duct 22. In addition, the metering valve 8 is opened so that compressed air can flow through the compressed air duct 21 and through the air duct 27 into the mixing chamber 13. The one-way valve or check valve 10 prevents the pressure from being inadvertently reduced by the turbine 9. In addition, the check valve 10 permits the patient to inhale at any time during the exhalation pause of the respiratory device. The remainder of the sequence corresponds to the sequence in the operating mode with the turbine 9 switched on. In this case, the microprocessor must, as part of its control, take into account the various inlet pressures in the control loops.

It is also possible with the respiratory device 1 to perform an emergency evacuation in order to prevent the occurrence of pressures that are hazardous to the patient, which can arise when using pressurized oxygen and/or compressed air. For the emergency evacuation, the pressure relief valve 15 is opened by the control valve 14 so that excess pressure can escape from the outlet duct 23.

Figure 2:
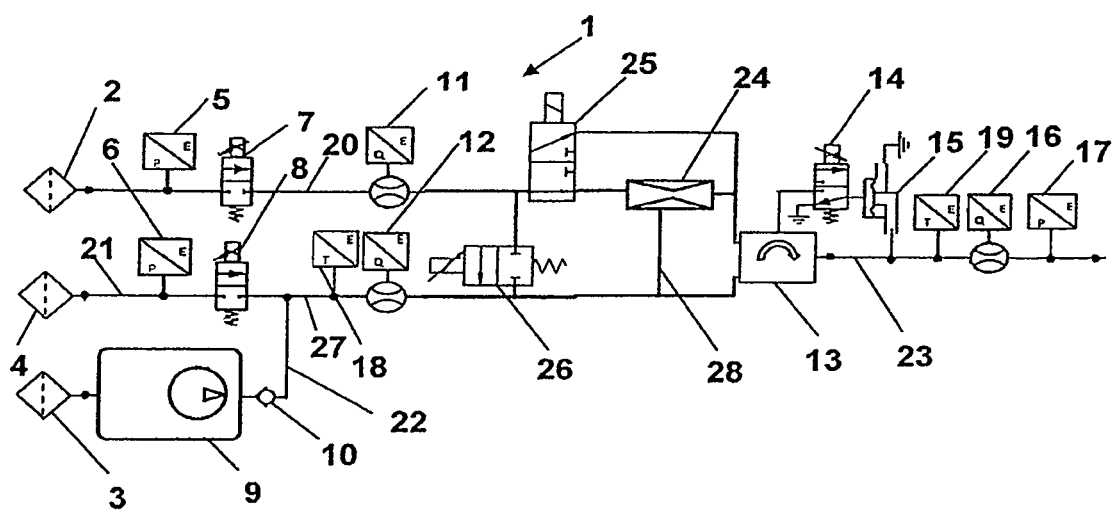
FIG. 2 is a respiratory device according to another embodiment of this invention.

FIG. 2 schematically shows a respiratory device 1 according to another exemplary embodiment of this invention. This embodiment largely corresponds to the embodiment from FIG. 1. The respiratory device 1 in this embodiment also has two metering valves 25, 26 and a venturi nozzle 24. The remaining components correspond to the components of the respiratory device 1 from FIG. 1 so that for their description, reference can be made to the description regarding FIG. 1.

By comparison with the respiratory device according to the embodiment from FIG. 1, in this exemplary embodiment, the metering valve 26 is positioned between the flow rate sensor 12 in the air duct 27 and the mixing chamber 13. In addition, the metering valve 25 and the venturi nozzle 24 are positioned in the oxygen duct 20 between the flow rate sensor 11 and the mixing chamber 13. The venturi nozzle 24 is also connected to the air duct 27 via an additional air duct 28.

In this embodiment, the respiratory device 1 can be used in a third operating mode, in which the respiratory device 1 is only connected to the oxygen supply at the oxygen inlet 2. No compressed air is connected to the compressed air inlet 4 and the metering valve 8 is closed. In addition, the turbine 9 is switched off. In this operating mode, the metering valve 25 is switched so that the oxygen is conveyed through the oxygen duct 20 by the venturi nozzle 24. As a result, a negative pressure is generated in the venturi nozzle 24, which aspirates ambient air via the air duct 28, the air duct 27, the ambient air duct 22, the switched-off turbine 9, and the intake opening 3 since the check valve 10 permits a flow of air from the intake opening 3 toward the mixing chamber 13. This aspirated ambient air travels via the air duct 27 into the mixing chamber 13 and is mixed with the oxygen from the oxygen duct 20. The pressure ratios in the venturi nozzle 24 determine the quantity of aspirated air and thus the oxygen concentration in the mixing chamber 13. The oxygen concentration can, for example, be regulated by the metering valve 26. In addition, reference can be made to the above statements about FIG. 1.

If a pressure drop is detected at one of the pressure sensors 5, 6, the turbine 9 can be automatically switched on in order, for example, to continue the artificial respiration when the compressed air is disconnected in order to transport a patient.

Figure 3:
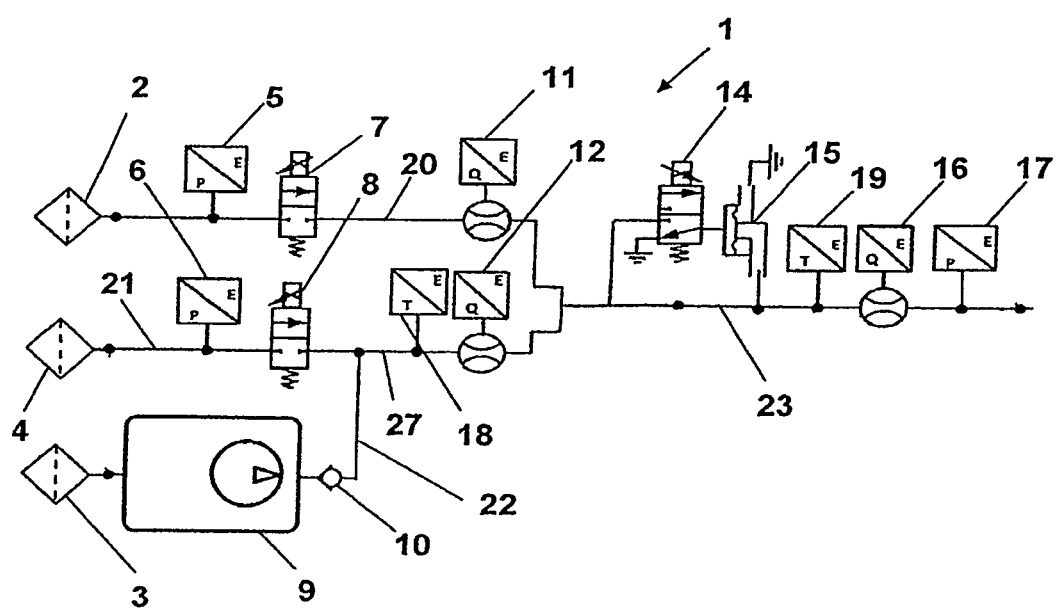
FIG. 3 is a respiratory device according to another embodiment of this invention.

FIG. 3 schematically shows a respiratory device 1 according to a third exemplary embodiment of this invention. This embodiment differs from the one shown in FIG. 1 because no mixing chamber is provided. Instead of this, the air duct 27 and the oxygen duct 20 feed into a shared outlet duct 23, which leads to the patient or more precisely, to the connection for the tube system for the patient. In this embodiment, the mixing of gases takes place in the outlet duct 23. This has the advantage that the respiratory device 1 requires a particularly small amount of space so that it is particularly suitable for mobile use.

Simply for the sake of clarity, it should be noted that the exemplary embodiments described above are merely intended to illustrate this invention and should not restrict the subject of this invention in any way.

The invention claimed is:

1. A respiratory device (1) for supplying a patient with respiratory air, having an oxygen inlet (2) for connecting to an oxygen supply and a compressed air inlet (4) for connecting to a compressed air supply, the respiratory device (1) comprising:
 a metering valve (7) for metering the supplied oxygen via the oxygen inlet (2),
 a turbine (9) for aspirating ambient air,
 a first pressure sensor (5) associated with the oxygen inlet (2) and configured to monitor a prevailing pressure at the oxygen inlet (2), and
 a second pressure sensor (6) associated with the compressed air inlet (4) and configured to monitor a prevailing pressure at the compressed air inlet (4),
 a control unit including a control loop, wherein the metering valve (7) and the turbine (9) are connected via the control loop to the first pressure sensor (5) for measuring the oxygen pressure, and to the second pressure sensor (6) for measuring the air pressure,
 wherein the metering valve (7) and the turbine (9) are controlled as a function of the measured oxygen pressure and the measured air pressure, and upon a pressure drop at the oxygen inlet (2) and/or the compressed air inlet (4) the control unit automatically switches on the turbine (9).

2. The respiratory device (1) according to claim 1, wherein the respiratory device (1) has a mixing chamber (13) and oxygen from the oxygen supply is mixed with the ambient air aspirated by the turbine (9) in the mixing chamber (13).

3. The respiratory device (1) according to claim 1, wherein oxygen from the oxygen supply and the ambient air aspirated by the turbine (9) or compressed air from a compressed air supply are mixed in an outlet duct (23) of the respiratory device (1).

4. The respiratory device (1) according to claim 3, wherein a flow rate and/or the pressure of the aspirated ambient air is regulated by a speed of the turbine (9).

5. The respiratory device (1) according to claim 4, wherein the respiratory device (1) operates in a first operating mode or in a second operating mode, in the first operating mode the turbine (9) aspirates ambient air and no compressed air is supplied and in the second operating mode compressed air is supplied from the compressed air supply and the turbine (9) switched off.

6. The respiratory device (1) according to claim 5, wherein the respiratory device (1) operates in a third operating mode, and in the third operating mode the turbine (9) is switched off and the compressed air supply is closed.

7. The respiratory device (1) according to claim 6, wherein the operating mode is automatically selected according to a predetermined priority and the respiratory device includes a manual selection to allow a user to cancel an automatic selection.

8. The respiratory device (1) according to claim 7, wherein in the first and second operating modes oxygen is supplied via the oxygen inlet (2).

9. The respiratory device (1) according to claim 8, wherein adjustments of a pressure, a flow pattern and/or a volume of the air aspirated by the turbine (9) are controlled by a microprocessor, and adjustments are adapted to be performed manually by a user or are automatically preset by a selected artificial respiration mode.

10. The respiratory device (1) according to claim 9, wherein the respiratory device (1) has a metering valve (7) for metering the supplied oxygen via the oxygen inlet (2), the metering valve (7) and the turbine (9) are connected via a control loop to a first flow rate meter (11) for measuring an oxygen flow rate and to a second flow rate meter (12) for measuring an air flow rate, and wherein the metering valve (7) and the turbine (9) are configured to be controlled as a function of the measured oxygen flow rate and/or the measured air flow rate.

11. The respiratory device (1) according to claim 10, wherein the respiratory device (1) has a check valve (10) permitting a flow of air from the turbine (9) toward the patient and a spontaneous respiration during an exhalation phase and prevents a flow of air toward the turbine (9).

12. The respiratory device (1) according to claim 11, wherein the respiratory device (1) has an emergency evacuation device (14, 15) allowing an excess pressure in the respiratory device (1) to be discharged.

13. The respiratory device (1) according to claim 12, wherein the respiratory device (1) has a venturi nozzle (24) configured so the oxygen from the oxygen inlet (2) flows through the venturi nozzle (24) and produces a negative pressure so ambient air is aspirated and is supplied for mixing with the oxygen.

14. The respiratory device (1) according to claim 13, wherein in the third operating mode, a supply of air is provided exclusively by the ambient air aspirated via the venturi nozzle (24).

15. The respiratory device (1) according to claim 1, wherein a flow rate and/or the pressure of the aspirated ambient air is regulated by a speed of the turbine (9).

16. The respiratory device (1) according to claim 1, wherein the respiratory device (1) operates in a first operating mode or in a second operating mode, in the first operating mode the turbine (9) aspirates ambient air and no compressed air is supplied and in the second operating mode compressed air is supplied from the compressed air supply and the turbine (9) switched off.

17. The respiratory device (1) according to claim 5, wherein the operating mode is automatically selected according to a predetermined priority and the respiratory device includes a manual selection to allow a user to cancel an automatic selection.

18. The respiratory device (1) according to claim 5, wherein in the first and second operating modes oxygen is supplied via the oxygen inlet (2).

19. The respiratory device (1) according to claim 1, wherein adjustments of a pressure, a flow pattern and/or a volume of the air aspirated by the turbine (9) are controlled by a microprocessor, and adjustments are adapted to be performed manually by a user or are automatically preset by a selected artificial respiration mode.

20. The respiratory device (1) according to claim 1, wherein the respiratory device (1) has a metering valve (7) for metering the supplied oxygen via the oxygen inlet (2), the metering valve (7) and the turbine (9) are connected via a control loop to a first flow rate meter (11) for measuring an oxygen flow rate and to a second flow rate meter (12) for measuring an air flow rate, and wherein the metering valve (7) and the turbine (9) are configured to be controlled as a function of the measured oxygen flow rate and/or the measured air flow rate.

21. The respiratory device (1) according to claim 1, wherein the respiratory device (1) has a check valve (10) permitting a flow of air from the turbine (9) toward the patient and a spontaneous respiration during an exhalation phase and prevents a flow of air toward the turbine (9).

22. The respiratory device (1) according to claim 1, wherein the respiratory device (1) has an emergency evacuation device (14, 15) allowing an excess pressure in the respiratory device (1) to be discharged.

23. The respiratory device (1) according to claim 1, wherein the respiratory device (1) has a venturi nozzle (24) configured so the oxygen from the oxygen inlet (2) flows through the venturi nozzle (24) and produces a negative pressure so ambient air is aspirated and is supplied for mixing with the oxygen.

24. The respiratory device (1) according to claim 1, further comprising:
   a flow rate meter (12) for measuring an air flow rate from the compressed air inlet (4) and/or the turbine (9), wherein the metering valve (7) and the turbine (9) are further controlled as a function of the measured air flow rate, and
   the turbine (9) connected between the second pressure sensor (6) and the flow rate meter (12) via a check valve (10), wherein the check valve (10) permits a flow of air from the turbine (9) toward the patient and a spontaneous respiration during an exhalation phase and prevents a flow of air toward the turbine (9).

25. The respiratory device (1) according to claim 24, further comprising:
   a compressed air duct (21) extending from the compressed air inlet (4),
   the flow rate meter (12) measuring the air flow rate in the compressed air duct (21), and
   the turbine (9) connected to the compressed air duct (21) between the second pressure sensor (6) and the flow rate meter (12) via the check valve (10).

* * * * *